United States Patent [19]
Bauer et al.

[11] Patent Number: 5,882,360
[45] Date of Patent: Mar. 16, 1999

[54] WATER-SOLUBLE COPPER PHTHALOCYANINE DYESTUFFS, THEIR PREPARATION AND THEIR USE

[75] Inventors: Wolfgang Bauer, Maintal; Dieter Baumgart, Egelsbach; Walter Zöller, Klingenberg; Klaus-Peter Kreutzer, Nidderau, all of Germany

[73] Assignee: Clariant GmbH, Frankfurt, Germany

[21] Appl. No.: 918,599

[22] Filed: Aug. 24, 1997

[30] Foreign Application Priority Data

Aug. 26, 1996 [DE] Germany .......................... 196 34 354.2

[51] Int. Cl.$^6$ .............................. D06P 1/14; C09B 47/04
[52] U.S. Cl. ................................ 8/661; 8/919; 106/31.47; 540/133; 540/134
[58] Field of Search .................... 540/133, 134; 8/661, 524, 527, 685, 919; 106/31.47

[56] References Cited

U.S. PATENT DOCUMENTS

| | | |
|---|---|---|
| 2,863,875 | 12/1958 | Bienert . |
| 4,024,096 | 5/1977 | Wachtel ............................ 260/29.3 |
| 4,024,397 | 5/1977 | Weiner .............................. 250/338 |
| 4,070,322 | 1/1978 | Hwang .............................. 524/364 |
| 4,111,650 | 9/1978 | Lacroix . |
| 4,379,710 | 4/1983 | Crounse ................................ 8/527 |
| 4,397,649 | 8/1983 | Springer . |

FOREIGN PATENT DOCUMENTS

| | | |
|---|---|---|
| 0596 383 A1 | of 0000 | European Pat. Off. . |
| 0 024 677 A1 | 3/1981 | European Pat. Off. . |
| 1117562 | 5/1956 | France . |
| 2316297 | 1/1977 | France . |
| A3411476 | of 0000 | Germany . |
| 190770 | of 0000 | Japan . |
| 1-190770 | 7/1989 | Japan . |
| 01297468 | 11/1989 | Japan . |
| 1 490 820 | 11/1977 | United Kingdom . |

OTHER PUBLICATIONS

Ullmann's Encyclopedia of Industrial Chemistry, Fifth, Completely Revised Edition /vol. A 13: "High–Performance Fibers to Imidazole and Derivatives".

JSDC Apr. 1973 (128–132): "Aggregation of Anionic Dyes in Aqueous Solutions".

Encyclopedia of Chemical Technology 3rd ed. (1982) V. 20, Kirk Othmer—Repography.

Chemistry and Technology of Printing and Imaging Systems: Blackie Academic & Professional, London, 1996.

*Primary Examiner*—Margaret Einsmann
*Attorney, Agent, or Firm*—Scott E. Hanf

[57] ABSTRACT

The present application relates to water-soluble copper phthalocyanine dyestuffs of the formula I

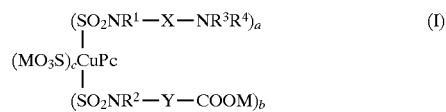

in which CuPc is a copper phthalocyanine radical;

X is a straight-chain or branched alkylene having 2 to 6 carbon atoms;

Y is a straight-chain or branched alkylene having 2 to 6 carbon atoms or a straight-chain or branched alkylene having 1 to 6 carbon atoms which is substituted by hydroxyl, carboxyl or amino;

$R^1$ and $R^2$ independently of one another are hydrogen or alkyl having 1 to 4 carbon atoms;

$R^3$ represents hydrogen, alkyl having 1 to 4 carbon atoms, hydroxyalkyl having 1 to 4 carbon atoms or aminoalkyl having 1 to 4 carbon atoms;

$R^4$ is hydrogen or alkyl having 1 to 4 carbon atoms;

M is a monovalent cation or one equivalent of a polyvalent cation;

a and b independently of one another are 1 or 2 and c is 0 or 1 the sum a+b+c being 3 or 4, processes for their preparation, their use for dyeing and printing naturally occurring and synthetic fiber materials, and recording liquids, in particular for the inkjet process, and liquid formulations for pulp-dyeing of paper which comprise the dyestuffs according to the invention.

12 Claims, No Drawings

WATER-SOLUBLE COPPER PHTHALOCYANINE DYESTUFFS, THEIR PREPARATION AND THEIR USE

The present application relates to water-soluble copper phthalocyanine dyestuffs, processes for their preparation, their use for dyeing and printing naturally occurring and synthetic fiber materials, and recording liquids, in particular for the inkjet process, and liquid formulations for pulp-dyeing of paper which comprise the dyestuffs according to the invention.

The inkjet process is a contact-less printing process in which droplets of the recording liquid are sprayed from one or more nozzles onto the medium to be printed. In order to obtain prints of high quality, i.e. high sharpness and clarity, the recording liquids and dyestuffs used for this purpose must meet high requirements, for example in respect of purity, absence of particles, viscosity, surface tension and corrosiveness, and in respect of solubility, tinctorial strength and fastness.

The inkjet process and the requirements on the recording liquids used therein are described, for example, in: Kirk-Othmer, Encyclopedia of Chemical Technology, 3rd Edition, Volume 20 (1982), 153–156; Ullmann's Encyclopedia of Industrial Chemistry, 5th Edition, Volume A 13 (1989), 588–594; and R. W. Kenyon, in P. Gregory, Chemistry and Technology of Printing and Imaging Systems, Blackie & Professional, London, 1996.

Dyestuffs for dyeing paper or celluloses in the pulp must meet high requirements in respect of substantivity and affinity for the cellulose fiber, and also in respect of tinctorial strength and fastness properties.

Water-soluble copper phthalocyanine dyestuffs are already known, but sometimes have considerable disadvantages for the abovementioned intended uses. For example, C.I. Direct Blue 199 and the dyestuffs mentioned in DE-A 34 11 476, EP-A 649889 and JP 1,190,770 are not optimum in respect of water-fastness and abrasion resistance for use in recording liquids.

C.I. Direct Blue 199, and the dyestuffs mentioned in EP-A 596383, U.S. Pat. No. 4,379,710, SU 491673 and JP 1,319,517 have disadvantages in the dyeing of paper or celluloses in the pulp, because their affinity for the cellulose fiber and their color yield are not adequate. As a result, a portion of the dyestuffs is found in the dyehouse wastewater, which is a disadvantage for economic and ecological reasons.

There is therefore a need for dyestuffs which do not have the disadvantages mentioned are therefore superior to the known dyestuffs.

Surprisingly, it has now been found that the requirements demanded are met by certain water-soluble copper phthalocyanine dyestuffs.

The present invention therefore relates to water-soluble copper phthalocyanine dyestuffs of the formula

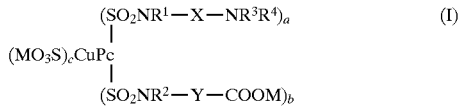
(I)

in which

CuPc is a copper phthalocyanine radical;

X is a straight-chain or branched alkylene having 2 to 6 carbon atoms;

Y is a straight-chain or branched alkylene having 1 to 6 carbon atoms or a straight-chain or branched alkylene having 1 to 6 carbon atoms which is substituted by hydroxyl, carboxyl or amino;

$R^1$ and $R^2$ independently of one another are hydrogen or alkyl having 1 to 4 carbon atoms;

$R^3$ represents hydrogen, alkyl having 1 to 4 carbon atoms, hydroxyalkyl having 1 to 4 carbon atoms or aminoalkyl having 1 to 4 carbon atoms;

$R^4$ is hydrogen or alkyl having 1 to 4 carbon atoms;

M is a monovalent cation or one equivalent of a polyvalent cation;

a and b independently of one another are 1 or 2 and c is 0 or 1 the sum a+b+c being 3 or 4.

X is, for example, ethylene, 1,2-propylene, 1,3-propylene, 2,2-dimethyl-1,3-propylene, 1,6-hexylene, 1,4-butylene or 1,4-pentylene. X is preferably alkylene having 2 to 4 carbon atoms.

Y is, for example, methylene, ethylene, ethane-1,1-diyl, propane-1,1-diyl, 1,2-propylene, hexylene, 2-methylpropane-1,1-diyl, 3-methylbutane-1,1-diyl, 2-methylbutane-1,1-diyl, 2-hydroxyethane-1,1-diyl, 2-carboxyethane-1,1-diyl, 3-carboxypropane-1,1-diyl, 5-aminopentane-1,1-diyl, 3-aminopropane-1,1-diyl or 4-aminobutane-1,1-diyl.

$R^1$ and $R^2$ independently of one another are, for example, hydrogen, methyl or ethyl. $R^1$ and $R^2$ are preferably hydrogen.

$R^3$ is, for example, hydrogen, methyl, ethyl, 2-aminoethyl or 2-hydroxyethyl. $R^3$ is preferably hydrogen or alkyl, hydroxyalkyl or aminoalkyl having in each case 1 or 2 carbon atoms.

$R^4$ is preferably hydrogen, methyl or ethyl. M is preferably a lithium, sodium, potassium or ammonium ion or an ammonium ion of the formula II $$R^5R^6R^7R^8N^{\oplus} \qquad (II)$$

in which $R^5$, $R^6$, $R^7$ and $R^8$ independently of one another are hydrogen, unsubstituted $(C_1-C_4)$-alkyl or $(C_1-C_4)$-alkyl which is substituted by one or more hydroxyl or 2-hydroxyethoxy groups. M moreover is preferably a mixture of the cations mentioned.

The sum a+b+c is preferably 4, where, particularly preferably, a and b are each 2 and c is 0.

The copper phthalocyanine dyestuffs of the formula I according to the invention can be prepared, for example, by reacting copper phthalocyaninesulfochlorides of the formula III $$CuPc(SO_2Cl)z \qquad (III)$$

in which z is 3 or 4, with alkylenediamines of the formula IV $$R^1HN-X-NR^3R^4 \qquad (IV)$$

in which $R^1$, $R^3$, $R^4$ and X are defined as stated above, and amino-alkylenecarboxylic acids of the formula V $$R^2HN-Y-COOH \qquad (V)$$

in which $R^2$ and Y are defined as stated above, at pH values from 7 to 14.

The copper phthalocyaninesulfochlorides of the formula III are preferably reacted with the alkylenediamines of the formula IV and the amino-alkylenecarboxylic acids of the formula V in a molar ratio of 1:1 to 1:2, particularly preferably in a molar ratio of 1:2. Any unreacted sulfochloride groups are hydrolyzed to sulfonic acid groups under the alkaline reaction conditions.

The reaction is preferably carried out in an aqueous medium at pH values from 8 to 11 and temperatures from −10° C. to 120° C., preferably from 5° C. to 60° C.

The compounds of the formulae III, IV and V are known and can be obtained commercially or prepared by methods known to the expert.

Alkylenediamines of the formula IV which can be employed in the process according to the invention are, for example ethylenediamine, 1,2-propylenediamine, 1,3-propylenediamine, 2,2-dimethyl-1,3-propylene-diamine, 1,6-hexylenediamine, N-ethylethylenediamine, N-methyl-1,3-propylenediamine, N,N-diethylethylenediamine, 3-dimethylamino-propylamine, 3-diethylaminopropylamine, N,N-diethyl-1,4-pentanediamine, diethylenetriamine, N-(2-aminoethyl)-1,3-propylenediamine, dipropylene-triamine, N,N-dimethyldipropylenetriamine or N-(2-aminoethyl)-ethanolamine.

Aminoalkylenecarboxylic acids of the formula V which can be employed in the process according to the invention are, for example, glycine, N-methylglycine, 2-aminopropionic acid, 3-aminopropionic acid, 2-aminobutyric acid, 3-aminobutyric acid, 6-aminohexanecarboxylic acid, valine, leucine, isoleucine, serine, aspartic acid, glutamic acid, lysine, 1,3-diaminobutyric acid or 1,4-diaminopentanecarboxylic acid.

The copper phthalocyanine dyestuffs of the formula I according to the invention can be isolated from the preferably aqueous reaction mixtures which initially result by customary methods of working up, for example by salting out, filtration or by spray drying, if appropriate after desalination by means of membrane filtration. However, an isolation can also be omitted and the reaction mixture comprising the dyestuffs of the formula I according to the invention can be converted directly into concentrated dyestuff solutions by addition of organic and/or inorganic bases and/or hydrotropic agents.

Possible inorganic or organic bases are, for example, lithium hydroxide, lithium carbonate, sodium hydroxide, sodium carbonate, sodium bicarbonate, potassium hydroxide, potassium carbonate, ammonia and organic amines, for example monoethanolamine, diethanolamine, triethanolamine, 2-aminopropanol, 3-aminopropanol, dipropanolamine, tripropanolamine, N-methylethanol, N,N-dimethylethanol, N-phenyl-propanol, ethylenediamine, tetramethylethylenediamine, tetramethyl-propylenediamine, tetramethylhexylenediamine, diethylenetriamine, triethylenetetramine or polyethyleneimine.

Hydrotropic compounds which can be employed are, for example, formamide, urea, tetramethylurea, ε-caprolactam, ethylene glycol, diethylene glycol, triethylene glycol, polyethylene glycol, propylene glycol, dipropylene glycol, polypropylene glycol, butylglycol, methylcellosolve, glycerol, N-methylpyrrolidone, 1,3-diethyl-2-imidazolidinone, sodium xylenesulfonate, sodium cumenesulfonate or sodium butylmonoglycol sulfate.

The present invention also relates to the use of water-soluble copper phthalocyanine dyestuffs of the formula I for dyeing and printing naturally occuring or synthetic fiber materials, in particular for recording script and images on various recording materials, and for dyeing paper or celluloses in the pulp.

The dyestuffs of the formula I according to the invention are particularly outstandingly suitable for the preparation of recording liquids, in particular of inks for the inkjet process, and also for other printing, duplicating, marking, writing, drawing, stamping or recording processes. Turquoise blue print images of excellent quality are obtained, these being distinguished by a very good brilliance and print sharpness and by a high fastness to light, abrasion resistance and fastness to water, also on normal, non-coated grades of paper. The compounds of the formula I are thus superior to both C.I. Direct Blue 199 and the dyestuffs mentioned in DE-A 34 11 476, EP-A 649889 and JP 1,190,770.

The present invention also relates to recording liquids which comprise one or more water-soluble copper phthalocyanine dyestuffs of the formula I. Such recording liquids are prepared by processes known per se. Data on compositions, in particular also those of inks for the inkjet printing process, are to be found, for example, in DE-A-21 32 324, DE-A-21 60 475, U.S. Pat. No. 4,024,096, U.S. Pat. No. 4,024,397 and U.S. Pat. No. 4,070,322. The precise composition of the recording liquid is of course adapted to suit the intended use.

The finished recording liquids in general comprise a total of 0.5 to 15% by weight (calculated in the dry state) of one or more soluble dyestuffs of the formula I, 0 to 99% by weight of water and 0.5 to 99.5% by weight of solvent and/or humectant. In a preferred embodiment, the finished recording liquids comprise 0.5 to 15% by weight of dyestuff (calculated in the dry state), 40 to 85% by weight of water and 10 to 50% by weight of solvent and/or humectant, and in another preferred embodiment they comprise 0.5 to 15% by weight of dyestuff (calculated in the dry state), 0 to 20% by weight of water and 70 to 99.5% by weight of solvent and/or humectant. The finished recording liquids as a rule also comprise further additives mentioned below.

Water used for the preparation of the recording liquids is preferably employed in the form of distilled or desalinated water. The solvent and/or humectant contained in the recording liquids can be an organic solvent or a mixture of such solvents, it being preferable to employ water-soluble solvents. Suitable solvents are, for example, mono- and polyhydric alcohols and ethers and esters thereof, thus, for example, alkanols, in particular having 1 to 4 carbon atoms, such as, for example, methanol, ethanol, propanol, isopropanol, butanol, isobutanol and tert-butanol; di- and trihydric alcohols, in particular those having 2 to 6 carbon atoms, for example ethylene glycol, propylene glycol, 1,3-propanediol, 1,4-butanediol, 1,5-pentanediol, 1,6-hexanediol, 1,2,6-hexanetriol, glycerol, diethylene glycol and dipropylene glycol; polyalkylene glycols, such as, for example, triethylene glycol, polyethylene glycol, tripropylene glycol and polypropylene glycol; lower alkyl ethers of polyhydric alcohols, such as, for example, ethylene glycol monomethyl or -ethyl or -propyl or -butyl ether, diethylene glycol monomethyl or -ethyl ether and triethylene glycol monomethyl or -ethyl ether; ketones and ketoalcohols, in particular those having 3 to 7 carbon atoms, such as, for example, acetone, methyl ethyl ketone, diethyl ketone, methyl isobutyl ketone, methyl pentyl ketone, cyclopentanone, cyclohexanone and diacetone alcohol; ethers, such as, for example, dibutyl ether, tetrahydrofuran and dioxane; esters, such as, for example, ethyl formate, methyl formate, methyl acetate, ethyl acetate, propyl acetate, butyl acetate, phenyl acetate, ethylene glycol monoethyl ether acetate and 2-hydroxyethyl acetate; amides, such as, for example, dimethylformamide, dimethylacetamide and N-methylpyrrolidone; and furthermore urea, tetramethylurea and thiodiglycol.

Some of the abovementioned substances not only act as solvents but also additionally display other properties. Thus, for example, the polyhydric alcohols also act as humectants.

The recording liquids can furthermore comprise customary additives, for example preservatives, such as, for example, phenol derivatives, cationic, anionic or nonionic surface-active substances (wetting agents), and agents for regulating the viscosity, for example polyvinyl alcohol and cellulose derivatives, or water-soluble naturally occurring or synthetic resins, as film-forming agents or binders for increasing the adhesive strength and abrasion resistance.

Amines, such as, for example, ethanolamine, diethanolamine, triethanolamine, N,N-dimethylethanolamine and diisopropylamine, serve chiefly to increase the pH of the recording liquid. They are as a rule present in the recording liquid to the extent of 0 to 10% by weight, preferably 0.5 to 5% by weight.

In the case of recording liquids for the inkjet printing process, depending on the embodiment of this printing process, for example as a continuous jet, intermittent jet, impulse jet or compound jet process, further additives can also be added if appropriate, for example for buffering the pH and for adjusting the electrical conductivity, the specific heat, the thermal expansion coefficient and the conductivity.

The recording liquids can be prepared in a simple manner by mixing the components, which can be carried out, for example, by dissolving one or more dyestuffs of the formula I in water and/or a solvent or also by diluting, to the desired extent, an aqueous solution obtained in the preparation of the dyestuff of the formula I, if appropriate after suitable preparation, and by then admixing further components, such as water, solvent, additives and the like.

No deposition of precipitates, which leads to blurred print images, occurs during storage of recording liquids according to the invention. Furthermore, during inkjet printing, no blocking of the nozzles occurs when the inks according to the invention are employed. In addition, no changes to the physical properties of inks according to the invention occur when they are used in an inkjet printer for a relatively long time with constant recirculation, or intermittently with the inkjet printer being switched off in the meantime.

The recording liquids according to the invention lie within the ranges suitable for the inkjet process in respect of viscosity and surface tension. They produce images of high optical density. They are suitable here for recording on various recording media, and on these give print images of excellent fastness to water, fastness to light, abrasion resistance and resolution.

In the dyeing of paper or celluloses in the pulp, brilliant turquoise blue dyeings which are distinguished by a high color strength and very good fastness properties, such as, for example, fastness to water, fastness to cylinder treatment, fastness to bleeding, fastness to acid, fastness to alkali and fastness to light are obtained with the dyestuffs of the formula I according to the invention.

It is particularly advantageous that the dyestuffs of the formula I according to the invention have a high substantivity and affinity for the cellulose fiber, so that ecologically favorable dyehouse waste waters which are practically colorless are obtained during papermaking. The dyestuffs of the formula I are thus superior to both C.I. Direct Blue 199 and the dyestuffs mentioned in EP-A 596383, U.S. Pat. No. 4,379,710, SU 491673 and JP 1,319,517.

The present invention also relates to concentrated liquid formulations for pulp-dyeing of paper which comprise one or more water-soluble copper phthalocyanine dyestuffs of the formula I. The liquid formulations for pulp-dyeing of paper preferably comprise 0.5 to 30% by weight, particularly preferably 10 to 20% by weight, of one or more dyestuffs of the formula I. The liquid formulations according to the invention can comprise hydrotropic compounds which are known per se, for example in an amount of 0.5 to 30% by weight. Suitable hydrotropic compounds are described, for example, in Melliand 43, 718 (1962), Angew.Chem. 63, 327 (1951), J. Soc. Dyers Col. 1973, 128 and Chemiker-Zeitung 96, 248 (1972).

The following examples serve to illustrate the invention without limiting it.

The contents data are percentages by weight.

EXAMPLE 1 a) Preparation of copper phthalocyanine-tetrasulfochloride 256.0 g of chlorosulfonic acid are initially introduced into the reaction vessel at 25° C. and 57.6 g of copper phthalocyanine are introduced. The mixture is then heated to 135° C. and is subsequently stirred until the evolution of gas has ended (4 hours). Thereafter, the mixture is cooled to 80° C., 120.1 g of thionyl chloride are metered in over a period of 2 hours and the mixture is subsequently stirred at 80° to 85° C. for 4 hours.

The reaction mixture, which has been cooled to 25° C., is then added slowly to a mixture to 150 ml of water and 300 g of ice. The precipitation temperature is kept at 0° to 5° C. by additional addition of ice.

The product suspension is then filtered and the filter cake is washed with 2.5 l of ice-water.

Yield: 255.0 g of copper phthalocyaninetetra-sulfochloride, moist, 38% pure.

b) 255 g of the copper phthalocyaninetetrasulfochloride prepared according to a) are introduced into a mixture of 200 ml of water and 200 g of ice and the pH is brought to 6.9 by addition of 13.3 g of sodium bicarbonate. A solution of 20.4 g of 3-dimethylaminopropylamine in 10 ml of water is then added, the mixture is initially subsequently stirred at 5° to 10° C. for 1 hour and a solution of 15.0 g of glycine in 15 ml of water and 15 ml of 10N sodium hydroxide solution is then added. The reaction mixture is subsequently stirred at 5° to 10° C. for 1 hour, at 20° to 25° C. for 3 hours and at 70°C. for 2 hours, the pH being kept in the range from 9 to 9.5 by addition of 52 g of 50% strength sodium hydroxide solution.

796 g of a 15% strength aqueous solution of the dyestuff of the formula

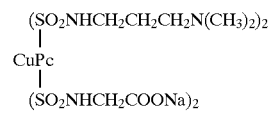

are obtained.

A salt-free solution of this dyestuff, which is suitable for the preparation of inks for the inkjet process, can be obtained by membrane filtration. Absorption spectrum in water: $\lambda_{max}$=607 nm, 670 nm.

EXAMPLE 2

60.0 g of N-methylpyrrolidone and 2.0 g of a commercially available preservative are added to 796.0 g of the dyestuff solution obtained according to Example 1b) and the mixture is brought to 1020.0 g with water. A 12% strength storage-stable solution of the dyestuff, which is outstandingly suitable for dyeing paper in the pulp, is obtained.

EXAMPLE 3

796.0 g of the dyestuff solution obtained according to Example 1b) are brought to pH 2.0 with 77.0 g of 32% strength hydrochloric acid. The dyestuff of the formula

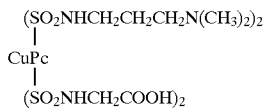

(SO$_2$NHCH$_2$CH$_2$CH$_2$N(CH$_3$)$_2$)$_2$
|
CuPc
|
(SO$_2$NHCH$_2$COOH)$_2$ which has precipitated out is filtered off and washed with 700 ml of desalinated water of 0° to 5° C. 314.4 g of a blue press-cake having a dry content of 35.1% are obtained, and are then stirred into 300 ml of desalinated water and dissolved at pH 6.8 with 40 ml of 5N lithium hydroxide solution. 654.4 g of an 18% strength storage-stable solution of the dyestuff of the formula

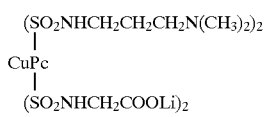

(SO$_2$NHCH$_2$CH$_2$CH$_2$N(CH$_3$)$_2$)$_2$
|
CuPc
|
(SO$_2$NHCH$_2$COOLi)$_2$ which is outstandingly suitable for the preparation of ink and recording liquids for the inkjet process, are obtained.

After the dyestuff solution has been dried, 104.0 g of a blue powder having a salt content of <0.1% of Li$_2$SO$_4$ and <0.1% of LiCl are obtained.

Comparison Example A 255.0 g of the copper phthalocyanine tetrasulfochloride obtained according to Example 1a) are introduced into a mixture of 200 ml of water and 200 g of ice and the pH is brought to 6.9 with 13.3 g of sodium bicarbonate. A solution of 15.0 g of glycine in 100 ml of water and 20 ml of 10N sodium hydroxide solution is then added and the mixture is subsequently stirred at 5° to 10° C. for 1 hour, 20° to 25° C. for 3 hours and 70° C. for 2 hours, the pH of the reaction mixture being kept at pH 9.5 to 9.7 with 10N sodium hydroxide solution. After the dyestuff solution has been dried at 80° C. in vacuo, 145.9 g of the dyestuff of the formula

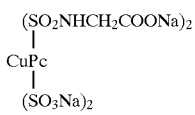

(SO$_2$NHCH$_2$COONa)$_2$
|
CuPc
|
(SO$_3$Na)$_2$ are obtained in the form of a blue crystalline powder having a purity of 84%.

Absorption spectrum in water: $\lambda_{max}$=625 nm, 663 nm.

Comparison Example B 255.0 g of the copper phthalocyanine tetrasulfochloride prepared according to Example 1a) are introduced into a mixture of 200 ml of water and 200 g of ice and the pH is brought to 6.9 with 13.3 g of sodium bicarbonate. 20.4 g of 3-dimethylaminopropylamine in 20 ml of water are then added and the mixture is subsequently stirred at 5° to 10° C. for 1 hour, 20° to 25° C. for 3 hours and 70° C. for 2 hours, the pH of the reaction mixture being kept at pH 9.5 to 9.7 by addition of 10N sodium hydroxide solution.

The resulting dyestuff solution is brought to pH 2 with 10N hydrochloric acid and the dyestuff acid which has precipitated out is isolated by filtration and washed with 300 ml of 0.1N hydrochloric acid.

390.0 g of a blue filter cake (dry content: 33.0%) are obtained and are then introduced into 500 ml of desalinated water, and the mixture is brought to pH 7.5 with 39.5 ml of 5N lithium hydroxide solution. After this dyestuff solution has been dried at 80° C. in vacuo, 104.0 g of the dyestuff of the formula

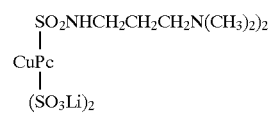

SO$_2$NHCH$_2$CH$_2$CH$_2$N(CH$_3$)$_2$)$_2$
|
CuPc
|
(SO$_3$Li)$_2$ are obtained in the form of a blue powder having a purity of 95%. Absorption spectrum in water: $\lambda_{max}$=614 nm, 662 nm.

EXAMPLE 4 a) Preparation of inks having a dyestuff content of 2.5%

In each case 2.5 g of pure dyestuff according to Example 3 and Comparison Examples A and B and of C.I. Direct Blue 199 are introduced and dissolved in a mixture of 20.0 g of diethylene glycol and 77.5 g of desalinated water at 25° C., while stirring.

b) Determination of the fastness to water

Ink streaks of the ink obtained according to a) are applied to normal paper and intermediately dried. Drops of water are then applied (80 μl) and left to act for 1 minute or 24 hours. The bleeding is evaluated as follows:

1= severe bleeding; 10= no bleeding.

The results can be seen from the following table

| Dyestuff | Fastness to water (1 minute) | Fastness to water (24 hours) |
| --- | --- | --- |
| Example 3 | 6 | 6 |
| Comparison Example A | 2 | 2 |
| Comparison Example B | 2 | 2 |
| CI Direct Blue 199 | 2 | 2 |

EXAMPLE 5

In each case 0.1 g of 100% pure dyestuff according to Example 3 and C.I. Direct Blue 199 is added to a mixture of 5 g of bleached cellulose and 250 ml of water, while stirring. After a reaction time of 5 minutes, 0.1 g of a commercially available fixing agent (®Solidogen FRZ, manufacturer: Hoechst AG) is added. After stirring for a further 5 minutes, a sheet is formed on a Rapid-Köthen sheet former and is then dried at 100° C.

Compared with the standard dyestuff C.I. Direct Blue 199, a considerably deeper dyeing is obtained with the dyestuff obtained according to Example 3.

The dyestuff obtained according to example 3 is furthermore also distinguished by a very low sensitivity to pH, while in the case of the standard dyestuff C.I. Direct Blue 199, marked changes in color shade result, depending on the pH.

Further dyestuffs according to the invention which can be prepared in accordance with the instructions of Example 3 can be seen in the following table.

$$(SO_2NR^1\text{—}X\text{—}NR^3R^4)_a$$
$$|$$
$$(MO_3S)_c CuPc$$
$$|$$
$$(SO_2NR^2\text{—}Y\text{—}COOM)_b$$

| Example | Compound of the formula (IV) | a | Compound of the formula (V) | b | c | Base | $\lambda_{max}$ (nm) |
|---|---|---|---|---|---|---|---|
| 6 | $NH_2CH_2CH_2N(CH_3)_2$ | 2 | $NH_2CHCH_3COOH$ | 2 | 0 | NaOH | 610, 665 |
| 7 | $NH_2CH_2CH_2CH_2N(CH_3)_2$ | 2 | $NH_2CH_2CH_2CH_2COOH$ | 2 | 0 | $H2NCH_2CH_2OH$ | 608, 655 |
| 8 | $NH_2CH_2CH_2NHCH_2CH_2NH_2$ | 2 | $NH_2CH_2COOH$ | 1 | 1 | LiOH | 607, 660 |
| 9 | $NH_2CH_2CH_2CH_2N(C_2H_5)_2$ | 2 | $NH_2CH_2COOH$ | 2 | 0 | $HN(CH_2CH_2OH)_2$ | 607, 653 |
| 10 | $NH_2CH_2CH_2CH_2NCH_2CH_2CH_2OH$ | 2 | $NH_2CH_2COOH$ | 2 | 0 | $N(CH_2CH_2OH)_3$ | 612, 659 |
| 11 | $NH(CH_3)CH_2CH_2CH_2N(CH_3)_2$ | 2 | $NH_2CH_2COOH$ | 2 | 0 | $N(CH_2CHOHCH_3)_3$ | 667, 660 |
| 12 | $NH_2CH_2CHCH_3N(CH_3)_2$ | 2 | $NH_2CH_2COOH$ | 2 | 0 | LiOH | 613, 665 |
| 13 | $NH_2CH_2CH_2CH_2N(CH_3)_2$ | 2 | $NH_2CH_2CH_2CH_2COOH$ | 1 | 1 | LiOH | 620, 661 |
| 14 | $NH_2CH_2CH_2CH_2N(CH_3)_2$ | 1 | $NH_2(CH_2)4CH(NH_2)COOH$ | 3 | 0 | LiOH | 613, 665 |
| 15 | $NH_2CH_2CH_2CH_2N(CH_3)_2$ | 2 | $NH_2COOHCHCH_2CH_2COOH$ | 2 | 0 | LiOH | 630, 666 |

We claim:

1. A water-soluble copper phthalocyanine dyestuff of the formula I $$(SO_2NR^1\text{—}X\text{—}NR^3R^4)_a$$
$$|$$
$$(MO_3S)_c CuPc$$
$$|$$
$$(SO_2NR^2\text{—}Y\text{—}COOM)_b$$

in which

CuPc is a copper phthalocyanine radical;

X is a straight-chain or branched alkylene having 2 to 6 carbon atoms;

Y is a straight-chain or branched alkylene having 1 to 6 carbon atoms or a straight-chain or branched alkylene having 1 to 6 carbon atoms which is substituted by hydroxyl, carboxyl or amino;

$R^1$ hydrogen or alkyl having 1 to 4 carbon atoms;

$R^2$ is hydrogen;

$R^3$ represents an alkyl having 1 to 4 carbon atoms, hydroxyalkyl having 1 to 4 carbon atoms or an aminoalkyl having 1 to 4 carbon atoms;

$R^4$ is hydrogen or an alkyl having 1 to 4 carbon atoms;

M is a monovalent cation or one equivalent of a polyvalent cation;

a and b independently of one another are 1 or 2; and c is 0 or 1 the sum a+b+c being 3 or 4.

2. A water-soluble copper phthalocyanine dyestuff as claimed in claim 1, in which X is alkylene having 2 to 4 carbon atoms.

3. A water-soluble copper phthalocyanine dyestuff as claimed in claim 1, in which $R^1$ and $R^2$ are hydrogen.

4. A water-soluble copper phthalocyanine as claimed in claim 1, in which $R^3$ is an alkyl, hydroxyalkyl or aminoalkyl having in each case 1 or 2 carbon atoms and $R^4$ is hydrogen, methyl or ethyl.

5. A water-soluble copper phthalocyanine dyestuff as claimed in claim 1, in which M is a lithium, sodium, potassium or ammonium ion or an ammonium ion of the formula II $$R^5R^6R^7R^8N^{\oplus} \qquad (II)$$

in which $R^5$, $R^6$, $R^7$ and $R^8$ independently of one another are hydrogen, unsubstituted $(C_1\text{–}C_4)$-alkyl or $(C_1\text{–}C_4)$-alkyl which is substituted by one or more hydroxyl or 2-hydroxyethoxy groups, or is a mixture of the cations mentioned.

6. A water-soluble copper phthalocyanine dyestuff as claimed in claim 1, wherein a and b are each 2 and c is 0.

7. A process for the preparation of a water-soluble copper phthalocyanine dyestuff which comprises:

reacting a copper phthalocyaninesulfochloride of the formula III $$CuPc(SO_2Cl)_z \qquad III$$

in which z is 3 or 4, with an alkylenediamine of the formula IV $$R^1HN\text{—}X\text{—}NR^3R^4 \qquad (IV)$$

in which;

$R^1$ is hydrogen or an alkyl group having 1 to 4 carbon atoms;

$R^3$ represents an alkyl having 1 to 4 carbon atoms, hydroxyalkyl having 1 to 4 carbon atoms or an aminoalkyl having 1 to 4 carbon atoms;

$R^4$ is hydrogen or an alkyl group having 1 to 4 carbon atoms;

X is a straight-chain or branched alkylene having 2 to 6 atoms;

and an aminoalkylenecarboxylic acid of the formula V $$R^2HN\text{—}Y\text{—}COOH \qquad (V)$$

in which;

$R^2$ is hydrogen;

Y is a straight-chain or branched alkylene having 10 to 6 carbon atoms or a straight-chain or branched alkylene having 1 to 6 carbon atoms which is substituted by hydroxyl, carboxyl or amino;

at pH values of 7 to 14.

8. A process for dyeing and printing fiber materials comprising the steps of:

providing a fibrous materials, said fibrous material being selected from the group of naturally occurring fibers, synthetic fibers or combinations thereof; and contacting said fibrous materials with a water-soluble copper phthalocyanine dyestuff to the formula I as claimed in claim 1.

9. A recording liquid, which comprises one or more water-soluble copper phthalocyanine dyestuffs of the formula I as claimed in claim 1.

10. A liquid formulation for pulp-dyeing of paper, which comprises one or more water-soluble copper phthalocyanine dyestuffs of the formula 1 as claimed in claim 1.

11. A process for recording script and images on a recording material comprising the steps of:

providing said recording material; and contacting said recording material with a water-soluble copper phthalocyanine dyestuff of the formula I as claimed in claim 1.

12. A process for dyeing paper or celluloses in the pulp, comprising the steps of:

providing paper or celluloses in pulp; and contacting said paper or celluloses in pulp with a water-soluble copper phthalocyanine dyestuff of the formula I as claimed in claim 1.

\* \* \* \* \*